US005273895A

United States Patent [19]
Rossi et al.

[11] Patent Number: 5,273,895
[45] Date of Patent: Dec. 28, 1993

[54] ENANTIOSELECTIVE PRODUCTION OF CHIRAL CARBOXYLIC ACIDS

[75] Inventors: Richard F. Rossi, Norton; Donald L. Heefner, Hudson; Charles M. Zepp, Berlin, all of Mass.

[73] Assignee: Sepracor, Inc., Marlborough, Mass.

[21] Appl. No.: 966,705

[22] Filed: Oct. 26, 1992

[51] Int. Cl.$^5$ .................. C12P 7/40; C12N 9/02
[52] U.S. Cl. ..................... 435/136; 435/189; 435/280
[58] Field of Search .................. 435/280, 136, 189

[56] References Cited

U.S. PATENT DOCUMENTS

| | | | |
|---|---|---|---|
| 4,800,162 | 1/1989 | Matson | 435/280 |
| 5,037,759 | 8/1991 | Clifford et al. | 435/280 |
| 5,057,427 | 10/1991 | Wald et al. | 435/280 |
| 5,077,217 | 12/1991 | Matson et al. | 435/280 |
| 5,089,405 | 2/1992 | Cerbelaud et al. | 435/280 |
| 5,108,917 | 4/1992 | Bertola et al. | 435/136 |

FOREIGN PATENT DOCUMENTS

| | | | |
|---|---|---|---|
| 0274146 | 11/1987 | European Pat. Off. | |
| 0426656 | 5/1991 | European Pat. Off. | 435/136 |
| 871558 | 2/1988 | Japan . | |
| 8909765 | 10/1989 | PCT Int'l Appl. | |
| 9004643 | 5/1990 | PCT Int'l Appl. | |
| 1160725 | 8/1969 | United Kingdom . | |

OTHER PUBLICATIONS

Patterson et al., "Enzymatic Conversion of α-Keto Aldehydes to Optically Active α-Hydroxy Acids Using Glyoxalase I and II," *J. Org. Chem.* 46, 4682–4685 (1981).

Shinkai et al., "Coenzyme Models. 26. Facile Oxidation of Aldehydes and α-Keto Acids by Flavin as Catalyzed by Thiazolium Ion and Cationic Micelle", *J. Org. Chem.* 45, 4947–4951, (1980).

Gu et al., "A Facile Enzymatic Resolution Process for the Preparation of (+)-S-2-(6-Methoxy-2-Naphthyl) Propionic Acid (Naproxen)", *Tet. Let.* 27, 1763–1766 (1986).

Yamamoto et al., "Production of S-(+)-Ibuprofen from a Nitrile Compound by Acinetobacter sp. Strain AK226," *App. Env. Microbiol.* 56, 3125–3129.

Primary Examiner—Douglas W. Robinson
Assistant Examiner—Jeffrey J. Sevigny
Attorney, Agent, or Firm—Heslin & Rothenberg

[57] ABSTRACT

A process for enantioselectively converting an aldehyde, a bisulfite adduct of an aldehyde or a glycidate to a chiral carboxylic acid is disclosed. The process utilizes a microorganism or an enzyme preparation from a microorganism and is particularly useful for producing NSAIDs of the profen class from readily available precursors. Preferred microorganisms are Gram-negative rod bacteria.

16 Claims, No Drawings

ENANTIOSELECTIVE PRODUCTION OF CHIRAL CARBOXYLIC ACIDS

BACKGROUND OF THE INVENTION

1. Field of the Invention

The invention relates to a process for enantioselectively producing a chiral carboxylic acid from a racemic precursor which is at the oxidation level of an aldehyde. The conversion of the precursor to the chiral carboxylic acid is accomplished by exposing the precursor to a microorganism or an enzyme preparation derived from a microorganism.

2. Information Disclosure

The oxidation of aldehydes to carboxylic acids is a classic manipulation of organic chemistry. However, typical chemical oxidants provide no selectivity among possible enantiomeric products when the starting material is racemic. It is known in other reactions that when an enzyme can be employed to carry out a conversion, it is sometimes found that the conversion is enantioselective. Thus, for example, Patterson et al. [*J. Org. Chem.* 46, 4682–4685 (1981)] describe the enzymatic conversion of α-ketoaldehydes to optically active α-hydroxyacids using glyoxalase I and glyoxalase II. The inventors are aware of no examples of the enantioselective conversion of racemic aldehydes to chiral carboxylic acids using microorganisms or enzymes therefrom.

The enantioselective conversion of racemic aldehydes to chiral acids would be a particularly useful process in the pharmaceutical industry, especially for the synthesis of single enantiomers of chiral acids of the NSAID class, such as ibuprofen, ketoprofen, naproxen and flurbiprofen. Among the NSAIDs, as among most drugs, one enantiomer of a racemic pair is often more active than the other in treating a medical condition. For ibuprofen, for example, it is the S form which is about 100 times as active as the R as an analgesic.

At present, pharmaceutical companies throughout the world are under pressure from the authorities that regulate drugs to supply all drugs in the pure, active form. The reason for this is that there is always a danger that one enantiomer of a drug may possess the desired activity and the other, although inactive in producing the desired activity, may possess extraneous and even harmful pharmacologic properties. This was most tragically demonstrated in the case of the drug thalidomide in which the S-form was an effective sedative but the R-enantiomer was a teratogen.

Methods for synthesizing or resolving ibuprofen to obtain the pure S enantiomer are known.

Yamamoto et al. [*Appl. Env. Microbiol.* 56, 3125–3129 (1990)] describe a synthesis of S-ibuprofen (Ia) in 95% enantiomeric excess (ee) from racemic 2-(4'-isobutylphenyl)propionitrile (II) using Acinetobacter.

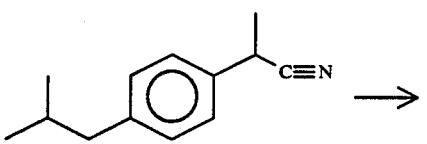

II

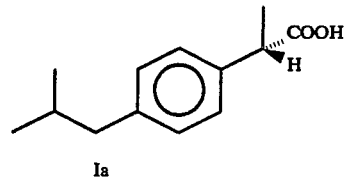

Ia

Cobbs et al. (U.S. Pat. No. 5,108,916) disclose a method for the enantioselective hydrolysis of fenoprofen (III) and ibuprofen (XV) methyl esters to yield the corresponding S-acids in 95% ee using lipase from *Candida rugosa*.

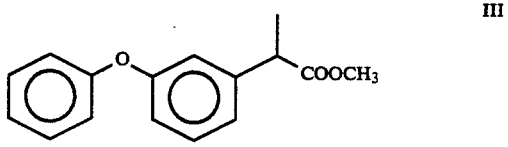

III

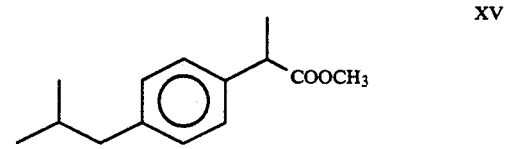

XV

A similar process is described for naproxen (IV) by Gu et al. [*Tet. Lett.* 27, 1763–1766 (1986)].

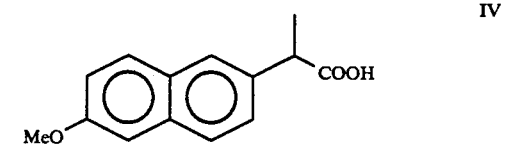

IV

Bertola et al. (U.S. Pat. No. 5,108,917) disclose a process for the preparation of ibuprofen enriched in the R-isomer from racemic ibuprofen methyl ester using Acetobacter, Bacillus and Staphylococcus.

Bertola et al. (European Application 274,146) disclose the preparation of greater than 70% S-naproxen by the microbially directed oxidation of 2-(6-methoxy-2-naphthyl)heptane(V). Microorganisms that were useful for the oxidation were found in the genera Exophiala and Rhinocladiella:

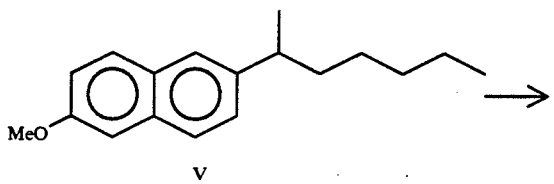

V

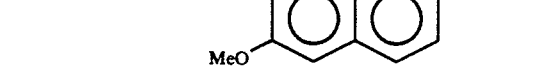

IV

Matson et al. (U.S. Pat. No. 5,077,217) and Wald et al. (U.S. Pat. No. 5,057,427) disclose a method for the enzymatic resolution of racemic esters in a membrane reactor. Exemplary water soluble esters are described for ibuprofen and naproxen. The preferred enzymes are alkaline proteases, esterases and lipases.

The foregoing methods appear to be useful for obtaining single isomers of phenylpropionic acid NSAIDs, also known as profens, from hydrolysis of nitriles, from hydrolysis of esters of the parent acid and even from α-oxidation of alkylbenzenes. The method presently used for the commercial production of racemic ibuprofen is described in British Patent 1,160,725 and is shown in scheme A:

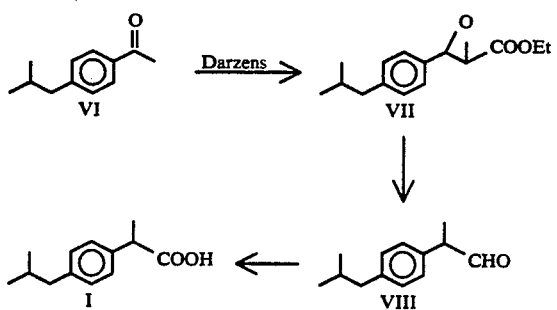

It will be noted that nitriles, esters of the parent acid and oxidizable alkylbenzenes do not occur among the intermediates. Thus the use of any of the existing methods to produce a single isomer of a profen entails steps additional to those employed in the production of its racemate.

There is thus a need for a chiral synthesis of ibuprofen that proceeds from an intermediate already available in the normal course of commercial production.

There is also a need for a chiral synthesis of other carboxylic acids that might be synthesized through an aldehyde intermediate.

SUMMARY OF THE INVENTION

It is an object of the invention to provide a method of enantioselectively converting a racemic aldehyde (e.g. VIII) or glycidic ester (e.g. VII) to a chiral carboxylic acid (e.g. Ia).

This and other objects, features and advantages are provided by the present invention which relates to a process for producing a single enantiomer or an enantiomer mixture enriched in a single enantiomer of a chiral carboxylic acid. The process comprises exposing a precursor chosen from aldehydes, bisulfite addition products of aldehydes, and glycidates to a microorganism or an enzyme preparation derived therefrom, whereby the precursor is converted to a single enantiomer or an enantiomeric mixture enriched in a single enantiomer of a chiral carboxylic acid. Preferably the microorganism is a bacterium; more preferably the microorganism is a Gram-negative rod bacterium. In particular, it has been found that microorganisms from the genera Pseudomonas, Aeromonas, Escherichia, Achromobacter and Alcaligenes are well-suited to carry out the conversion.

In the case where the precursor is an aldehyde or bisulfite addition product, a preferred enzyme preparation contains a dehydrogenase, referred to in the IUB nomenclature as an oxidoreductase. Preferably the carboxylic acid is chosen from the group consisting of ibuprofen, naproxen, ketoprofen and flurbiprofen, most preferably the carboxylic acid is ibuprofen and the single enantiomer is S-ibuprofen. When the desired product is ibuprofen, one precursor is α-methyl-4-(2-methylpropyl)benzeneacetaldehyde (VIII) and the preferred microorganisms are *Pseudomonas paucimobilis* and *Alcaligenes faecalis;* another precursor is an α-hydroxy-β-methyl-4-(2-methylpropyl)benzenethanesulfonate salt (XII) and the preferred microorganism is *Pseudomonas paucimobilis;* yet another precursor is a 3-methyl-3-[4-(2-methylpropyl)phenyl]oxirane-2-carboxylate salt (XIII) and the preferred microorganism is *Pseudomonas paucimobilis*.

In another aspect, the invention relates to a process for the enantioselective conversion of a precursor of formula IX:

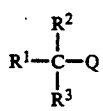

to a carboxylic acid of formula X:

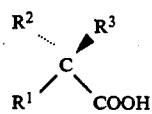

wherein
R$^1$ is alkyl, aralkyl, aryl or substituted aryl;
R$^2$ is hydrogen, alkyl, aralkyl, aryl or substituted aryl;
R$^3$ is hydrogen, alkyl, aralkyl, aryl or substituted aryl;
Q is —CHO or

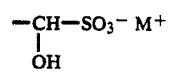

M+ is an alkali metal or ammonium ion; and
R$^1$, R$^2$, and R$^3$ are different. The process comprises subjecting the precursor to the action of a microorganism or enzyme preparation derived therefrom that will enantioselectively convert it to a carboxylic acid.

The graphic representations of racemic, ambiscalemic, and scalemic or enantiomerically pure compounds used herein are taken from Maehr *J. Chem. Ed.* 62, 114–120 (1985). Thus, solid and broken wedges (e.g. Ia) are used to denote the absolute configuration of a chiral element; wedge outlines and dotted or broken lines (e.g. X) denote enantiomerically pure compounds of indeterminate absolute configuration.

In a preferred embodiment R$^1$ is substituted aryl, R$^2$ is methyl and R$^3$ is hydrogen.

In a particularly preferred embodiment, R$^1$ is 4-(2-methylpropyl)phenyl.

In another aspect the invention relates to a process for the enantioselective conversion of a precursor of formula XI

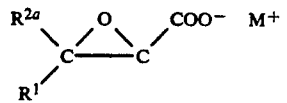

to a carboxylic acid of formula Xa

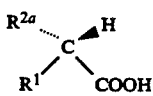

Xa wherein
$R^1$ is alkyl, aralkyl, aryl or substituted aryl;
$R^{2a}$ is alkyl, aralkyl, aryl or substituted aryl;
$M^+$ is an alkali metal or ammonium ion; and
$R^1$ and $R^{2a}$ are different. The process comprises subjecting the precursor to the action of a microorganism or enzyme preparation derived therefrom that will enantioselectively convert it to a carboxylic acid. In a preferred embodiment $R^1$ is substituted aryl, most preferably $R^1$ is 4-(2-methylpropyl)phenyl, and $R^{2a}$ is methyl.

In another aspect the invention relates to a process for the enantiospecific conversion of a racemic aldehyde or an aldehyde equivalent to a substantially optically pure profen comprising:

(a) growing a plurality of colonies of microorganisms in an aqueous medium on a substrate;
(b) overlaying the colonies with an opaque aqueous medium containing the sparingly soluble aldehyde or aldehyde equivalent in suspension, or the soluble aldehyde equivalent (bisulfite adduct or glycidate) in solution, and continuing to grow the microorganisms;
(c) making an initial selection of those colonies over which the opaque medium has become transparent or vice versa;
(d) incubating the aldehyde or aldehyde equivalent with cultures of each of the initially selected colonies whereby the aldehyde or aldehyde equivalent is converted to a profen;
(e) determining the enantiomeric ratio of the isomers of the profen as produced;
(f) making a second selection of the cultures based on the enantiomeric ratio; and
(g) incubating the aldehyde or aldehyde equivalent with a culture of the second selected cultures whereby the aldehyde or aldehyde equivalent is converted to a substantially optically pure profen. Aldehydes or aldehyde equivalents are for example, VIII, XII, and XIII:

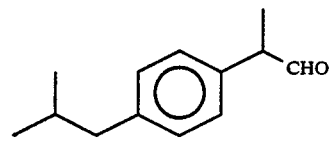

VIII

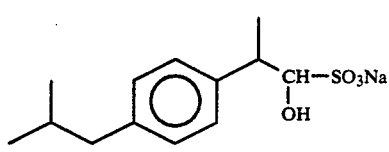

XII and

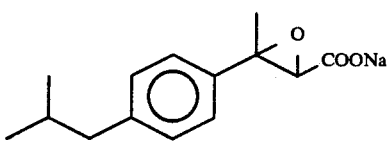

XIII

Step (f) of making a second selection of the cultures in one preferred embodiment selects those cultures producing the highest yield of substantially pure S-ibuprofen, and in another preferred embodiment selects those cultures producing the highest yield of substantially pure R-ibuprofen.

Preferred microorganisms for all of the aspects of the invention are bacteria, in particular Gram-negative rod bacteria. Representatives of the genera Pseudomonas, Aeromonas, Escherichia, Achromobacter and Alcaligenes are preferred and *Pseudomonas paucimobilis* and *Alcaligenes faecalis* are most preferred.

DETAILED DESCRIPTION

The present invention encompasses a method for converting a racemic precursor in the oxidation state of an aldehyde to a chiral carboxylic acid. The precursor may be the aldehyde corresponding to the acid, in which case the conversion is formally an oxidation, or the precursor may be a glycidic acid, in which case the conversion comprises both a decarboxylation and a formal oxidation.

The racemic precursor will usually be a mixture of enantiomers at a chiral center α- to the site which is being formally oxidized. However, this is not a necessary condition; the chiral center could, in principle, be located at another position in the precursor molecule.

Microorganisms capable of carrying out the transformations described above have been found among Gram-negative rod bacteria: Pseudomonas, Aeromonas, Escgerichia, Achromobacter and Alcaligenes, but it is expected that other genera, for example, Aspergillus, Bacillus, Mucor, Penicillium, Rhizopus, Serratia, Staphylococcus, Streptococcus, Streptomyces, Tritirachium, Chromobacterium and Geotrichium will also provide species and strains capable of carrying out the conversion. In addition, fungi and yeasts, such as Candida and Saccharomyces may also be used.

A particularly rapid and efficient method of selecting a microorganism capable of transforming a sparingly water-soluble aldehyde (such as a profen precursor)into an appreciably more water soluble acid salt (such as a profen salt) takes advantage of the change in solubility brought about by the transformation. Thus, a suspension of the aldehyde in an aqueous medium, such as agarose, is exposed to a colony or colonies of a microorganism, and the initially opaque medium is observed for signs of translucence or transparence in the vicinity of a colony. Colonies producing transparency in the aqueous medium containing the sparingly soluble precursor are then selected for larger scale incubation using standard microbiological techniques.

Alternatively, if the precursor is water-soluble (e.g. a bisulfite addition product) a solution of the soluble precursor in agarose can be laid down over the colonies and the initially clear medium can be observed for signs of opacity. The terms "sparingly soluble" and "water-soluble" as used herein refer to whether a compound produces a clear solution at about 2 g/L at the pH to which the solution is buffered. Thus sparingly soluble compounds produce an opaque suspension or a precipitate; soluble compounds produce a clear solution.

On the larger scale, the products of the incubation are isolated by appropriate and well-known chemical procedures and are examined for the presence of the desired optical isomer of the carboxylic acid. The analysis may be carried out by any of the standard techniques known in the art; we have found that HPLC on a chiral substrate is particularly useful for the rapid semi-quantitative analysis of large numbers of samples. For the profens, a Chiralcel OJ ™ column available from Daicel Chemical Industries, Ltd. (Japan) is well-suited.

In an embodiment of the invention, the microorganisms capable of enantioselective conversion of precursor into a carboxylic acid may be selected from a natural source. A number of microorganisms isolated from natural sources, particularly from soil samples, were selected according to the above screening procedure, and when subjected to further tests as hereinafter described, showed their ability for enantioselective conversion. Microorganisms capable of the conversion may also be identified by applying the same selection process to samples obtained from the American Type Culture Collection (ATCC) (Rockville, MD). Also microorganisms that have acquired the ability for enantioselective conversion through the introduction of foreign genetic material are encompassed in the above definition. This can be accomplished by transferring the cloned gene encoding a polypeptide responsible for the enantioselective conversion, e.g. an enzyme, from one suitable microorganism to another microorganism, particularly to *Escherichia coli*. Transformed microorganisms may belong to the genera Pseudomonas, Mycobacterium, Streptomyces, Saccharomyces, Kluyveromyces, Bacillus, Nocardia, Rhodococcus, Escherichia and Corynebacterium.

The microorganisms may advantageously be immobilized for example on a polymer gel. This can be done with living cells, killed cells and/or resting cells, or with suitable enzymes derived therefrom, which may be purified to a certain extent if a higher specific activity is needed.

Therefore by the term "microorganisms or substances derived therefrom" is meant the microorganisms, killed, alive or resting, and extracts therefrom such as enzymes or metabolites, optionally concentrated, purified and immobilized. For example, enzymes optionally in combination with, for example, artificial or natural co-factors, may be used. Enzymes derived from living cells or killed cells may produce the desired isomer under suitable conditions. The microorganisms or substances derived therefrom may be used several times. Even without a co-substrate (for example glucose) the microorganisms may remain active. The enrichment in the desired optical isomer may take place in suitable buffers as well as in physiological salts.

The procedure for selecting the microorganism follows the sequence of:
(a) growing a plurality of colonies of microorganisms in an aqueous medium on a substrate. The preferred medium is Brain-Heart Infusion (BHI) and the preferred substrate is agar coated on a plate;
(b) overlaying the colonies with an aqueous medium, preferably agarose buffered to pH 7.0 with phosphate buffer containing the aldehyde or aldehyde equivalent in suspension or solution. The organisms are allowed to continue to grow under the aldehyde layer;
(c) making an initial selection of those colonies over which the opaque medium has become transparent or the transparent medium opaque. This constitutes the primary selection.

A secondary selection is then made by
(a) incubating the aldehyde or aldehyde equivalent with cultures of each of the initially selected colonies; and
(b) determining the enantiomeric ratio of the isomers of carboxylic acid as produced.

The colonies that appear from the analysis of the second selection to produce the largest amounts of the desired enantiomer are then used for the preparative conversions.

According to a preferred embodiment of the present invention, a microorganism having the ability to convert the precursor of a profen into a profen may be cultured for about 0.5 to 10 days. The cells may be then suspended in a liquid nutrient medium and the precursor subjected to the action of the cells. Alternatively, the cells may be killed, for example, by suspending in a lysis medium, and the precursor then may be subjected to the action of the substances released from the lysed cells.

After the abovementioned cultivation for about 0.5 to 10 days, the cells may be isolated from the culturing medium before they are suspended in the liquid nutrient medium or in a lysis medium.

To grow the microorganisms used for the selective oxidation of the precursor of ibuprofen, ordinary culture media containing an assimilable carbon source (for example glucose, lactose, sucrose, etc.), a nitrogen source (for example ammonium sulphate, ammonium nitrate, ammonium chloride, etc.), with an agent providing an organic nutrient source (for example yeast extract, malt extract, peptone, meat extract, etc.) and an inorganic nutrient source (for example phosphate, magnesium, potassium, zinc, iron and other metals in trace amounts) may be used.

A Jap medium optionally enriched with one or more ingredients may be used as suitable culture medium. Another culture medium is a TSB-medium 2X, optionally enriched with one or more ingredients. A medium consisting of 60 g/l trypticase soy broth (Oxoid ®) may be used. Another medium is 2XTY optionally enriched with one or more ingredients. A medium consisting of Tryptone (Difco ®) 30 g/l, Yeast extract (Difco ®) 20 g/l, NaCl 3 g/l, $(NH_4)_2HPO_4$ 1 g/l and $(NH_4)_2SO_4$ 1 g/l at pH 6.8 can be used. Another culture medium is a skimmed milk medium optionally enriched with one or more ingredients.

A preferred medium is a BHI medium containing 37 g/L of BHI and 15 g/L of agar adjusted to pH 7.0.

A temperature of 0° to 45° C. and a pH of 3.5 to 9 is preferably maintained during the growth of the microorganisms. More preferably the microorganisms are grown at a temperature of 20° to 37° C. and at a pH of 5 to 9.

The aerobic conditions required during the growth of the microorganisms can be provided according to any of the well established procedures, provided that the supply of oxygen is sufficient to meet the metabolic requirement of the microorganisms. This is most conveniently achieved by supplying oxygen, suitably in the form of air and optionally at the same time shaking or stirring the reaction liquid. During the conversion of precursor to the carboxylic acid the microorganisms can be in a growing stage using an above-mentioned ordinary culture medium or can be preserved in any system (medium or buffer) preventing degradation of enzymes.

The carboxylic acid produced by the microorganisms or substances derived therefrom, as mentioned above, can be recovered and purified according to any of the procedures known per se for such products.

The microorganisms can be kept on agar slants, frozen in 50% glycerol or lyophilized. If required, precultures of these microorganisms can be made according to any of the well-established procedures, for example the microorganisms can be incubated in bouillon or in BHI for 24 hours at 30° C. in a rotary shaker.

In the case where the chiral center is α- to the carboxylate, the reaction of aldehydes and bisulfites can be represented schematically as the conversion of a precursor of formula

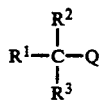

to a carboxylic acid of formula

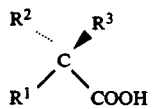

wherein
R$^1$ is alkyl, aralkyl, aryl or substituted aryl;
R$^2$ is hydrogen, alkyl, aralkyl, aryl or substituted aryl;
R$^3$ is hydrogen, alkyl, aralkyl, aryl or substituted aryl;
Q is —CHO or

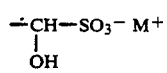

M$^+$ is an alkali metal or ammonium ion; and
R$^1$, R$^2$, and R$^3$ are different.

Alternately, the reaction of glycidates can be represented as the conversion of a precursor of formula

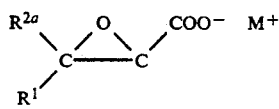

to a carboxylic acid of formula

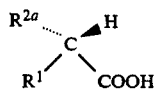

wherein R$^{2a}$ is aryl, aralkyl, aryl or substituted aryl; and R$^1$ and R$^{2a}$ are different.

Throughout the specification substituents are defined when introduced and retain that definition in all subsequent occurrences. Alkyl refers to linear, branched or cyclic hydrocarbon residues of one to six carbons; aryl refers to phenyl, naphthyl and the like residues; aralkyl refers to aryl residues linked to alkylene chains (e.g. benzyl, phenethyl, α-methylphenethyl, etc.); substituted aryl refers to phenyl or naphthyl substituted with one or more alkyl, alkoxy, phenyl, phenoxy, benzoyl, halogen and similar substituents (e.g. 4-isobutylphenyl; 6-methoxy-2-naphthyl; 3-fluoro-4-phenyl; 3-phenoxyphenyl; 3-benzoylphenyl 3-chloro-4-(2,5-dihydro-1H-pyrrol-1-yl)phenyl; 4-(2-thienylcarbonyl)phenyl; 4-(1,3-dihydro-1-oxo-2H-isoindol-2-yl)phenyl). In preferred embodiments where the product is a profen, R$^2$ or R$^{2a}$ will be methyl.

In the cases where the chiral carbon is activated toward deprotonation and one substituent on the chiral carbon is hydrogen, it may be possible to racemize the chiral center under conditions that do not substantially inhibit the activity of the microorganism or enzyme mixture. In such a case, the process may be carried out essentially to complete conversion of a racemic precursor to a single enantiomer of a carboxylic acid. Toward this end, deprotonation experiments were carried out on the bisulfite addition product of ibuprofen (XII), and it was found that deuterium was incorporated onto the chiral carbon at pH 8.9 and above. Thus, an in situ racemization step may be included in the microorganism-catalyzed conversion process and the precursor XII thereby substantially completely converted to a single isomer of ibuprofen.

Two series of experiments were carried out using the precursors VIII, XII and XIII of ibuprofen and the bisulfite precursor of 2-phenylpropionic acid XIV. In the first series of experiments, a number of microorganisms obtained from soil samples and from ATCC were streaked and plated as described above. Organisms indicated as having source A were from the ATCC. Their ATCC identification numbers are indicated in parentheses. Organisms designated as having source B were originally from ATCC colonies, but have become laboratory contaminants; organisms designated as having source C were obtained from soil samples in Marlboro, Massachusetts. After growing for 48 to 72 hours on BHI/agar, the test colonies were overlaid with a 2.0 g/L solution of precursor XII in agarose containing 20 mM phosphate buffer at pH 7.0. The colonies were grown for a further one to two weeks and observed for zones of opacity. Those colonies exhibiting zones of opacity were then further cultured in the second series of experiments as follows: The organism was inoculated into 25 mL of sterile BHI broth in a 125 mL shaker flask and the flask was shaken at 150 RPM and at 25 degrees C. After 24 hours 10 mg of precursor VIII, XII, XIII or XIV was added in an aqueous suspension to each flask. The flask was returned to the shaker and shaken an additional 48-72 hours. After incubation, 3 mL of well mixed broth was removed, acidified to pH 2, and extracted with 2 mL of diethyl ether. The ether solution was placed in an HPLC vial with 2 mL of mobile phase and a sample injected onto a Chiralcel OJ ™ column. The column was eluted with a mobile phase consisting of 0.5% acetic acid in hexane. The results are shown in Tables A, B, C and D. The numbers in the columns R and S represent peak areas from HPLC and are dimensionless, relative numbers. They are used both to derive a ratio of R to S (shown in columns four and five) and to roughly quantify the extent of conversion under the standard conditions.

TABLE A

2-Phenylpropionic Acid From the Bisulfite Adduct XIV

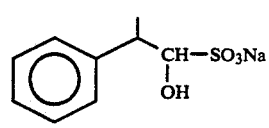

| Organism | Source | R | S | Normalized R | Normalized S |
|---|---|---|---|---|---|
| Ps. paucimobilis | C | 0 | 0 | 0 | 0 |
| A. faecalis | B(3525) | 14664 | 0 | 1.00 | 0 |
| Ps. fluorescens | C | 21012 | 12571 | 0.63 | 0.37 |

TABLE A-continued
2-Phenylpropionic Acid From the Bisulfite Adduct XIV

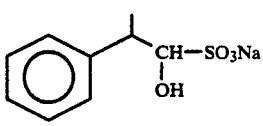

| Organism | Source | R | S | Normalized R | Normalized S |
|---|---|---|---|---|---|
| Ps. testo/alcal. | A(21192) | 6761 | 8114 | 0.45 | 0.55 |
| Ps. fluorescens | C | 19803 | 17923 | 0.53 | 0.47 |
| Ps. luteola | B(11291) | 93982 | 0 | 1.00 | 0 |
| Ps. putida | C | 0 | 0 | 0 | 0 |
| A. faecalis | A(21283) | 0 | 0 | 0 | 0 |
| Ps. fluorescens | A(29574) | 14945 | 11654 | 0.56 | 0.44 |
| Achromobacter sp. | A(25289) | 0 | 0 | 0 | 0 |
| Ae. salmonicida | C | 91181 | 91181 | 0 | 1.00 |
| A. faecalis | A(8750) | 3301 | 10729 | 0.24 | 0.76 |

TABLE B
Ibuprofen From the aldehyde VIII

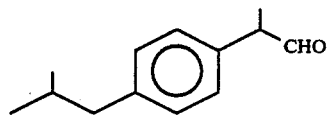

| Organism | Source | R | S | Normalized R | Normalized S |
|---|---|---|---|---|---|
| Ps. paucimobilis | C | 0 | 13440 | 0 | 1.00 |
| A. faecalis | B(3525) | 0 | 0 | 0 | 0 |
| Ps. fluorescens | C | 21620 | 0 | 1.00 | 0 |
| Ps. testo/alcal. | A(21192) | 17405 | 43009 | 0.29 | 0.71 |
| Ps. fluorescens | C | 0 | 0 | 0 | 0 |
| Ps. luteola | B(11291) | 0 | 0 | 0 | 0 |
| Ps. putida | C | 36996 | 33636 | 0.52 | 0.48 |
| A. faecalis | A(21283) | 0 | 14843 | 0 | 1.00 |
| Ps. fluorescens | A(29574) | 24772 | 0 | 1.00 | 0 |
| Ae. salmonicida | C | 0 | 0 | 0 | 0 |
| A. faecalis | A(8750) | 57979 | 0 | 1.00 | 0 |
| E. coli | B(31022) | 0 | 0 | 0 | 0 |

TABLE C
Ibuprofen from the Bisulfite Adduct XII

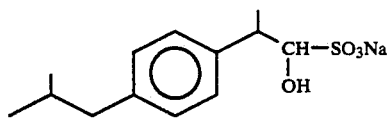

| Organism | Source | R | S | Normalized R | Normalized S |
|---|---|---|---|---|---|
| Ps. paucimobilis | C | 0 | 58761 | 0 | 1.00 |
| A. faecalis | B(3525) | 0 | 7743 | 0 | 1.00 |
| Ps. fluorescens | C | 13113 | 0 | 1.00 | 0 |
| Ps. testo/alcal. | A(21192) | 13890 | 20341 | 0.41 | 0.59 |
| Ps. fluorescens | C | 6199 | 0 | 1.00 | 0 |
| Ps. luteola | B(11291) | 0 | 0 | 0 | 0 |
| Ps. putida | C | 0 | 0 | 0 | 0 |
| A. faecalis | A(21283) | 48846 | 0 | 1.00 | 0 |
| Ps. fluorescens | A(29574) | 26971 | 0 | 1.00 | 0 |
| Ae. salmonicida | C | 0 | 11103 | 0 | 1.00 |
| A. faecalis | A(8750) | 40250 | 0 | 1.00 | 0 |
| E. coli | B(31022) | 0 | 10989 | 0 | 1.00 |

TABLE D
Ibuprofen from the Glycidate XIII

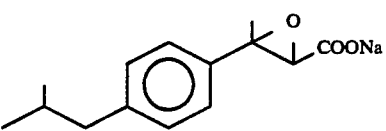

| Organism | Source | R | S | Normalized R | Normalized S |
|---|---|---|---|---|---|
| Ps. paucimobilis | C | 0 | 69525 | 0 | 1.00 |
| A. faecalis | B(3525) | 30138 | 0 | 1.00 | 0 |
| Ps. fluorescens | C | 9945 | 4993 | 0.67 | 0.33 |
| Ps. testo/alcal. | A(21192) | 47075 | 0 | 1.00 | 0 |
| Ps. fluorescens | C | 81739 | 5666 | 0.94 | 0.06 |
| Ps. luteola | B(11291) | 0 | 5082 | 0 | 1.00 |
| Ps. putida | C | 9879 | 4413 | 0.69 | 0.31 |
| A. faecalis | A(21283) | 0 | 0 | 0 | 0 |
| Ps. fluorescens | A(29574) | 16660 | 0 | 1.00 | 0 |
| Ae. salmonicida | C | 0 | 14734 | 0 | 1.00 |
| A. faecalis | A(8750) | 19002 | 0 | 1.00 | — |
| E. coli | B(31022) | 21795 | 7439 | 0.75 | 0.25 |

A deposit of the *Pseudomonas paucimobilis* (SEP54) used in the foregoing experiments has been made with the American Type Culture Collection, Rockville, Maryland, under the deposit number ATCC 55369.

While the invention has been particularly shown and described with reference to preferred embodiments thereof, it will be understood by those skilled in the art that other changes in form and details may be made therein without departing from the spirit and scope of the invention.

We claim:

1. A process for the enantioselective conversion of a precursor of formula

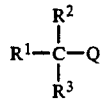

to a carboxylic acid of formula

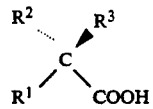

wherein
$R^1$ is alkyl, aralkyl, aryl or substituted aryl;
$R^2$ is hydrogen, alkyl, aralkyl, aryl or substituted aryl;
$R^3$ is hydrogen, alkyl, aralkyl, aryl or substituted aryl;
Q is —CHO or

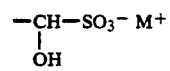

$M^+$ is an alkali metal or ammonium ion; and
$R^1$, $R^2$, and $R^3$ are different
comprising subjecting said precursor to the action of a microorganism or an enzyme preparation derived therefrom capable of oxidizing said precursor to said carboxylic acid wherein said microorganism is selected from the genera Pseudomonas, Aeromonas, Escherichia, and Alcaligenes.

2. A process according to claim 1 further characterized in that said enzyme preparation contains an oxidoreductase.

3. A process according to claim 1 wherein said carboxylic acid is selected from the group consisting of ibuprofen, naproxen, ketoprofen and flurbiprofen.

4. A process according to claim 3 wherein said carboxylic acid is ibuprofen.

5. A process according to claim 4 wherein said single enantiomer of ibuprofen is S-ibuprofen.

6. A process according to claim 5 wherein said precursor is α-methyl-4-(2-methylpropyl)benzeneacetaldehyde.

7. A process according to claim 6 wherein said microorganism is *Pseudomonas paucimobilis* or *Alcaligenes faecalie*.

8. A process according to claim 5 wherein said precursor is an α-hydroxy-β-methyl-4-(2-methylpropyl)-benzenethanesulfonate salt.

9. A process according to claim 8 wherein said microorganism is *Pseudomonas paucimobilis*.

10. A process according to claim 1 wherein $R^1$ is substituted aryl, $R^2$ is methyl and $R^3$ is hydrogen.

11. A process according to claim 10 wherein $R^1$ is 4-(2-methylpropyl)phenyl.

12. A process for the enantioselective conversion of a precursor of formula

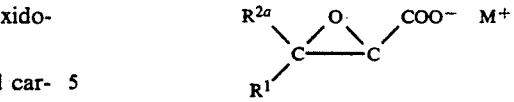

to a carboxylic acid of formula

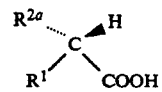

wherein
$R^1$ is alkyl, aralkyl, aryl or substituted aryl;
$R^{2a}$ is alkyl, aralkyl, aryl or substituted aryl;
$M^+$ is an alkali metal or ammonium ion; and
$R^1$ and $R^{2a}$ are different
comprising subjecting said precursor to the action of a microorganism or an enzyme preparation derived therefrom capable of converting said precursor to said carboxylic acid wherein said microorganism is selected from the genera Pseudomonas, Aeromonas, Escherichia, and Alcaligenes.

13. A process according to claim 12 wherein said precursor is a 3-methyl-3-[4-(2-methylpropyl)phenyl-]oxirane-2-carboxylate salt.

14. A process according to claim 13 wherein said microorganism is *Pseudomonas paucimobilis*.

15. A process according to claim 12 wherein $R^1$ is substituted aryl and $R^{2a}$ is methyl.

16. A process according to claim 12 wherein $R^1$ is 4-(2-methylpropyl)phenyl.

* * * * *